(12) United States Patent
Kostrzewski

(10) Patent No.: US 8,397,972 B2
(45) Date of Patent: *Mar. 19, 2013

(54) SHIPPING WEDGE WITH LOCKOUT

(75) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/051,276

(22) Filed: Mar. 18, 2011

(65) Prior Publication Data
US 2012/0234894 A1 Sep. 20, 2012

(51) Int. Cl.
*A61B 17/068* (2006.01)
(52) U.S. Cl. .............. 227/175.2; 227/19; 227/175.3; 227/176.1
(58) Field of Classification Search ............. 227/19, 227/175.1, 176.1, 180.1, 175.2, 175.3; 606/139, 606/219
See application file for complete search history.

(56) References Cited

U.S. PATENT DOCUMENTS

| | | | |
|---|---|---|---|
| 3,079,606 A | 3/1963 | Bobrov et al. | |
| 3,315,863 A * | 4/1967 | O'Dea | 227/19 |
| 3,490,675 A | 1/1970 | Green et al. | |
| 3,499,591 A | 3/1970 | Green | |
| 4,244,372 A | 1/1981 | Kapitanov et al. | |
| 4,429,695 A | 2/1984 | Green | |
| 4,520,817 A | 6/1985 | Green | |
| 4,576,167 A | 3/1986 | Noiles | |
| 4,589,413 A | 5/1986 | Malyshev et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,664,305 A | 5/1987 | Blake et al. | |
| 4,672,964 A | 6/1987 | Dee et al. | |
| 4,715,520 A | 12/1987 | Roehr, Jr. et al. | |
| 4,763,669 A | 8/1988 | Jaeger | |
| 4,819,853 A | 4/1989 | Green | |
| 4,863,088 A | 9/1989 | Redmond et al. | |
| 4,880,015 A | 11/1989 | Nierman | |
| 4,892,244 A | 1/1990 | Fox et al. | |
| 4,924,864 A | 5/1990 | Danzig | |

(Continued)

FOREIGN PATENT DOCUMENTS

| DE | 4300307 | 7/1994 |
|---|---|---|
| DE | 202 17 850 | 1/2003 |

(Continued)

*Primary Examiner* — Scott A. Smith

(57) ABSTRACT

A loading unit having a shipping safety device is provided for use with a surgical instrument. The loading unit includes a body portion, a movable operative device disposed in the body portion and an actuator associated with the body portion and operable to move the movable operative device. A locking member movably mounted in the body portion and movable in response to movement of the actuator. The locking member is movable between a first locked position and a second unlocked position. The removable safety device generally includes a base, a blocking member projecting from the base and engageable with the movable operative device and a lockout member projecting from the base and engageable with the locking member. Flexible arms extend from the base and engage the body portion of the loading unit. The removable safety device is locked to the body portion when the locking member is in the first locked position and is unlocked for removal from the body portion when the locking member it is in the second unlocked position.

20 Claims, 16 Drawing Sheets

U.S. PATENT DOCUMENTS

| | | | |
|---|---|---|---|
| 4,978,049 A | 12/1990 | Green | |
| 4,991,764 A | 2/1991 | Mericle | |
| 5,014,899 A | 5/1991 | Presty et al. | |
| 5,040,715 A | 8/1991 | Green et al. | |
| 5,065,929 A | 11/1991 | Schulze et al. | |
| 5,071,052 A | 12/1991 | Rodak et al. | |
| 5,071,430 A | 12/1991 | De Salis et al. | |
| 5,074,454 A | 12/1991 | Peters | |
| 5,083,695 A | 1/1992 | Foslien et al. | |
| 5,104,025 A | 4/1992 | Main et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,144,942 A | 9/1992 | Decarie et al. | |
| 5,152,279 A | 10/1992 | Wilk | |
| 5,156,315 A | 10/1992 | Green et al. | |
| 5,180,092 A | 1/1993 | Crainich | |
| 5,209,747 A | 5/1993 | Knoepfler | |
| 5,275,608 A | 1/1994 | Forman et al. | |
| 5,282,826 A | 2/1994 | Quadri | |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,330,502 A | 7/1994 | Hassler et al. | |
| 5,332,142 A | 7/1994 | Robinson et al. | |
| 5,350,391 A | 9/1994 | Iacovelli | |
| 5,354,311 A | 10/1994 | Kambin et al. | |
| 5,358,506 A | 10/1994 | Green et al. | |
| 5,366,133 A | 11/1994 | Geiste | |
| 5,366,477 A | 11/1994 | LeMarie, III et al. | |
| 5,374,277 A | 12/1994 | Hassler | |
| 5,376,095 A | 12/1994 | Ortiz | |
| 5,379,933 A | 1/1995 | Green et al. | |
| 5,383,888 A | 1/1995 | Zvenyatsky et al. | |
| 5,389,098 A | 2/1995 | Tsuruta et al. | |
| 5,397,046 A | 3/1995 | Savage et al. | |
| 5,397,324 A | 3/1995 | Carroll et al. | |
| 5,403,312 A | 4/1995 | Yates et al. | |
| 5,413,268 A | 5/1995 | Green et al. | |
| 5,415,334 A | 5/1995 | Williamson, IV et al. | |
| 5,415,335 A | 5/1995 | Knodel, Jr. | |
| 5,423,471 A | 6/1995 | Mastri et al. | |
| 5,433,721 A | 7/1995 | Hooven et al. | |
| 5,452,837 A | 9/1995 | Williamson, IV et al. | |
| 5,465,895 A | 11/1995 | Knodel et al. | |
| 5,467,911 A | 11/1995 | Tsuruta et al. | |
| 5,474,566 A | 12/1995 | Alesi et al. | |
| 5,474,571 A | 12/1995 | Lang | |
| 5,484,451 A | 1/1996 | Akopov et al. | |
| 5,486,185 A | 1/1996 | Freitas et al. | |
| 5,487,500 A | 1/1996 | Knodel et al. | |
| 5,507,426 A | 4/1996 | Young et al. | |
| 5,535,935 A | 7/1996 | Vidal et al. | |
| 5,551,622 A | 9/1996 | Yoon | |
| 5,562,241 A | 10/1996 | Knodel et al. | |
| 5,582,617 A | 12/1996 | Klieman et al. | |
| 5,597,107 A | 1/1997 | Knodel et al. | |
| 5,601,573 A | 2/1997 | Fogelberg et al. | |
| 5,605,272 A | 2/1997 | Witt et al. | |
| 5,630,539 A | 5/1997 | Plyley et al. | |
| 5,634,584 A | 6/1997 | Okorocha et al. | |
| 5,651,491 A | 7/1997 | Heaton et al. | |
| 5,653,373 A | 8/1997 | Green et al. | |
| 5,655,698 A | 8/1997 | Yoon | |
| 5,662,258 A | 9/1997 | Knodel et al. | |
| 5,662,259 A | 9/1997 | Yoon | |
| 5,662,260 A | 9/1997 | Yoon | |
| 5,673,841 A | 10/1997 | Schulze et al. | |
| 5,680,982 A | 10/1997 | Schulze et al. | |
| 5,681,330 A | 10/1997 | Hughett et al. | |
| 5,715,988 A | 2/1998 | Palmer | |
| 5,718,359 A | 2/1998 | Palmer et al. | |
| 5,762,255 A | 6/1998 | Chrisman et al. | |
| 5,794,834 A | 8/1998 | Hamblin et al. | |
| 5,797,537 A | 8/1998 | Oberlin et al. | |
| 5,800,449 A | 9/1998 | Wales | |
| 5,820,009 A | 10/1998 | Melling et al. | |
| 5,893,506 A | 4/1999 | Powell | |
| 5,901,895 A | 5/1999 | Heaton et al. | |
| 5,911,352 A | 6/1999 | Racenet et al. | |
| 5,984,938 A | 11/1999 | Yoon | |
| 5,988,479 A | 11/1999 | Palmer | |
| 5,993,465 A | 11/1999 | Shipp et al. | |
| 6,010,054 A | 1/2000 | Johnson et al. | |
| 6,032,849 A | 3/2000 | Mastri et al. | |
| 6,050,472 A | 4/2000 | Shibata | |
| 6,079,606 A | 6/2000 | Milliman et al. | |
| 6,109,500 A | 8/2000 | Alli et al. | |
| 6,119,913 A | 9/2000 | Adams et al. | |
| 6,131,789 A | 10/2000 | Schulze et al. | |
| 6,174,309 B1 | 1/2001 | Wrublewski et al. | |
| 6,241,139 B1 | 6/2001 | Milliman et al. | |
| 6,241,140 B1 | 6/2001 | Adams et al. | |
| 6,585,144 B2* | 7/2003 | Adams et al. | 227/175.1 |
| 6,601,749 B2 | 8/2003 | Sullivan et al. | |
| 6,607,540 B1 | 8/2003 | Shipp | |
| 6,755,338 B2 | 6/2004 | Hahnen et al. | |
| 6,805,273 B2 | 10/2004 | Bilotti et al. | |
| 6,978,921 B2 | 12/2005 | Shelton, IV et al. | |
| 6,988,650 B2 | 1/2006 | Schwemberger et al. | |
| 7,000,818 B2 | 2/2006 | Shelton, IV et al. | |
| 7,055,730 B2* | 6/2006 | Ehrenfels et al. | 227/175.4 |
| 7,055,731 B2 | 6/2006 | Shelton, IV et al. | |
| 7,134,587 B2 | 11/2006 | Schwemberger et al. | |
| 7,140,527 B2* | 11/2006 | Ehrenfels et al. | 227/175.1 |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,210,609 B2 | 5/2007 | Leiboff et al | |
| 7,278,563 B1 | 10/2007 | Green | |
| RE40,237 E | 4/2008 | Bilotti | |
| 7,380,696 B2 | 6/2008 | Shelton, IV et al. | |
| 7,407,078 B2 | 8/2008 | Shelton, IV et al. | |
| 7,434,717 B2 | 10/2008 | Shelton, IV et al. | |
| 7,451,904 B2 | 11/2008 | Shelton, IV | |
| 7,464,849 B2 | 12/2008 | Shelton, IV et al. | |
| 7,503,474 B2 | 3/2009 | Hillstead et al. | |
| 7,568,604 B2* | 8/2009 | Ehrenfels et al. | 227/178.1 |
| 7,780,055 B2* | 8/2010 | Scirica et al. | 227/175.2 |
| 8,225,979 B2* | 7/2012 | Farascioni et al. | 227/175.2 |
| 2005/0070758 A1 | 3/2005 | Wells et al. | |
| 2005/0139636 A1 | 6/2005 | Schwemberger et al. | |
| 2005/0145672 A1 | 7/2005 | Schwemberger et al. | |
| 2005/0184124 A1 | 8/2005 | Scirica et al. | |
| 2005/0247752 A1 | 11/2005 | Kelly et al. | |
| 2005/0247753 A1 | 11/2005 | Kelly et al. | |
| 2006/0144898 A1 | 7/2006 | Bilotti et al. | |
| 2006/0226195 A1 | 10/2006 | Scirica et al. | |
| 2007/0029364 A1 | 2/2007 | Kruszynski et al. | |
| 2007/0039995 A1 | 2/2007 | Schwemberger et al. | |
| 2007/0039996 A1 | 2/2007 | Mather et al. | |
| 2007/0039997 A1 | 2/2007 | Mather et al. | |
| 2007/0114261 A1 | 5/2007 | Ortiz et al. | |
| 2007/0175950 A1 | 8/2007 | Shelton, IV et al. | |
| 2007/0181631 A1 | 8/2007 | Bilotti et al. | |
| 2007/0219563 A1 | 9/2007 | Voegele | |
| 2007/0221702 A1 | 9/2007 | Kruszynski | |
| 2007/0246508 A1 | 10/2007 | Green | |
| 2007/0255296 A1 | 11/2007 | Sauer | |
| 2008/0027466 A1 | 1/2008 | Vitali et al. | |
| 2008/0093415 A1 | 4/2008 | Bilotti | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0272171 A1 | 11/2008 | Viola | |
| 2008/0302854 A1 | 12/2008 | Rethy et al. | |
| 2009/0008424 A1 | 1/2009 | Green | |
| 2009/0134199 A1 | 5/2009 | Heinrich et al. | |
| 2009/0206131 A1 | 8/2009 | Weisenburgh, II et al. | |
| 2009/0272784 A1 | 11/2009 | Farascioni | |
| 2010/0072258 A1 | 3/2010 | Farascioni et al. | |

FOREIGN PATENT DOCUMENTS

| | | |
|---|---|---|
| EP | 0484677 | 5/1992 |
| EP | 0537498 A2 | 4/1993 |
| EP | 0589306 | 3/1994 |
| EP | 0591946 | 4/1994 |
| EP | 0592243 | 4/1994 |
| EP | 0621009 | 10/1994 |
| EP | 0656188 | 6/1995 |
| EP | 1550410 A2 | 7/2005 |
| EP | 1908413 A1 | 4/2008 |
| FR | 2681775 | 10/1991 |
| WO | WO 03/022133 A2 | 3/2003 |

\* cited by examiner

SHIPPING WEDGE WITH LOCKOUT

BACKGROUND

1. Technical Field

The present disclosure relates to a shipping safety device for use with a surgical instrument. More particularly, the present disclosure relates to a shipping wedge having a lockout member and a single use loading unit or "SULU" having a lockout mechanism for use with the surgical instrument.

2. Background of Related Art

In an effort to reduce trauma and recovery time, many surgical procedures are performed through small openings in the skin, such as an incision or a natural body orifice. Generally, such procedures are referred to as "endoscopic," unless performed on the patient's abdomen, in which case the procedure is referred to as "laparoscopic." Throughout the present disclosure, the term "minimally invasive" should be understood to encompass both endoscopic and laparoscopic procedures.

During the course of minimally invasive surgical procedures, a surgical fastener applying apparatus is often employed to connect adjacent sections of tissue. Many varieties of such apparatus are known in the art, some of which are specifically adapted for use in particular surgical procedures including, but not limited to, end-to-end anastomosis, circular end-to-end anastomosis, open gastrointestinal anastomosis, endoscopic gastrointestinal anastomosis, and transverse anastomosis. Examples of suitable surgical fastener applying apparatus are disclosed in U.S. Pat. Nos. 5,915,616; 6,202,914; 5,865,361; and 5,964,394. Typically, these surgical fastener applying apparatus include a first member that is movable relative to a second member such that target tissue is positionable therebetween to facilitate grasping and/or clamping of the target tissue.

Linear surgical fastener applying apparatus generally include two elongated jaw members, one of which includes a surgical fastener cartridge housing a plurality of surgical fasteners that are arranged in two or more linear rows, and the other of which includes an anvil component with a plurality of fastener forming pockets that are configured and dimensioned to receive and form the surgical fasteners upon ejection of the fasteners from the surgical fastener cartridge. The surgical fastener applying apparatus may also include a knife that is movable between the linear rows of surgical fasteners such that the tissue being joined and/or sealed is simultaneously, or sequentially, cut upon actuation of the surgical fastener applying apparatus. Given this capability, surgical fastener applying apparatus of the linear variety are commonly used during surgical procedures to simultaneously seal and cut target tissue, e.g., a patient's vasculature, organs, or the like.

Some surgical fastener applying apparatus are provided in two parts, a reusable handle or actuator section and a removable or replaceable single use loading unit or "SULU". The SULU includes the staple containing cartridge, anvil and a knife blade for cutting stapled tissue.

Safety devices may be provided to prevent movement of the knife blade during shipment and/or prior to use. In some instances, the safety devices can be removed from the SULU prior to the SULU being assembled to the reusable handle. Therefore, there exists a need for a shipping safety device and SULU having locking structure which prevents removal of the shipping safety device from the SULU prior to assembly with a reusable handle.

SUMMARY

There is disclosed a shipping wedge for use with a surgical instrument having body portion. The shipping wedge includes a base, a blocking member depending from the base and engagable with a movable operative member of the surgical instrument and a locking member also depending from the base and engageable with a lockout mechanism of the surgical instrument. Flexible arms project from the base and are shaped to cooperate with the body portion of the surgical instrument.

In certain embodiments, the locking member includes an enlarged flange in the form of a circular disc. A downward extension connects the circular disc to the base. The blocking member is a distally facing hook engageable with the movable operative member of the surgical instrument.

In certain embodiments, the flexible arms are a first flexible arm and a second flexible arm depending from opposed sides of the base and engageable with a body portion of the surgical instrument. The first and second flexible arms are longitudinally spaced along the base.

An alignment unit is located at a distal end of the base and includes a pair of distally projecting, flexible arms for aligning the blocking member with corresponding structure on the surgical instrument.

In one embodiment, the shipping wedge further includes second and third flexible arms depending from opposed sides of the base and longitudinally spaced from the first and second flexible arms.

A grasping frame is provided and extends from a side of the base opposite of the locking member. An indicia plate is located between the grasping frame and the base for display of various modes of informational indicia. In a specific embodiment, a flexible thumb tab extends from a proximal end of the grasping frame.

In one embodiment, the shipping wedge is foamed from a polymeric material while in an alternative embodiment, the shipping wedge is formed from a metallic material.

In a particular embodiment, the shipping wedge is formed as a monolithic structure.

There is also disclosed a surgical instrument having a lockout mechanism, including a body portion, an actuator movably mounted on the body portion. A lockout mechanism, including a locking plate, is movably mounted to the body portion. The instrument includes a loading lock having a locking member, the locking plate being engageable with the locking member of the loading lock, the locking plate being movable in response to movement of the actuator between a locked position preventing removal of the loading lock from the body portion to an unlocked position allowing removal of the loading lock from the body portion, the loading lock having flexible arms shaped to cooperate with the body portion of the instrument.

In a specific embodiment, the locking plate includes a keyhole slot engageable with the shipping safety device. The keyhole slot includes a first narrower locking portion and a second enlarged unlocking portion.

The locking plate is operatively connected to the actuator by an extension rod and is biased to the locked position by a biasing spring mounted in the body portion.

In certain embodiments, the body portion has a knife member and the loading lock has a hook insertable through a hole defined in the body portion and arranged to block movement of the knife member.

There is further disclosed a loading unit having a removable shipping safety device. The loading unit generally includes a body portion, a movable operative device disposed in the body portion and an actuator associated with the body portion and operable to move the movable operative device. A locking member movably mounted in the body portion and movable in response to movement of the actuator. The locking member is movable between a first locked position and a second unlocked position.

The removable shipping safety device generally includes a base, a blocking member projecting from the base and engageable with the movable operative device and a lockout member projecting from the base and engageable with the locking member. The removable safety device is locked to the body portion when the locking member is in the first locked position and is unlocked for removal from the body portion when the locking member it is in the second unlocked position.

In a particular embodiment, the locking member includes a keyhole slot engageable with the lockout member of the removable safety device such that the removable safety device is locked to the body portion when the lockout member is in a keyway in the locking member and is unlocked from the body portion when the lockout member is in a hole formed in the locking member.

DESCRIPTION OF THE DRAWINGS

An embodiment of the presently disclosed shipping wedge with lockout is disclosed herein with reference to the drawings, wherein.

DETAILED DESCRIPTION OF EMBODIMENTS

An embodiment of the presently disclosed shipping wedge with lockout will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
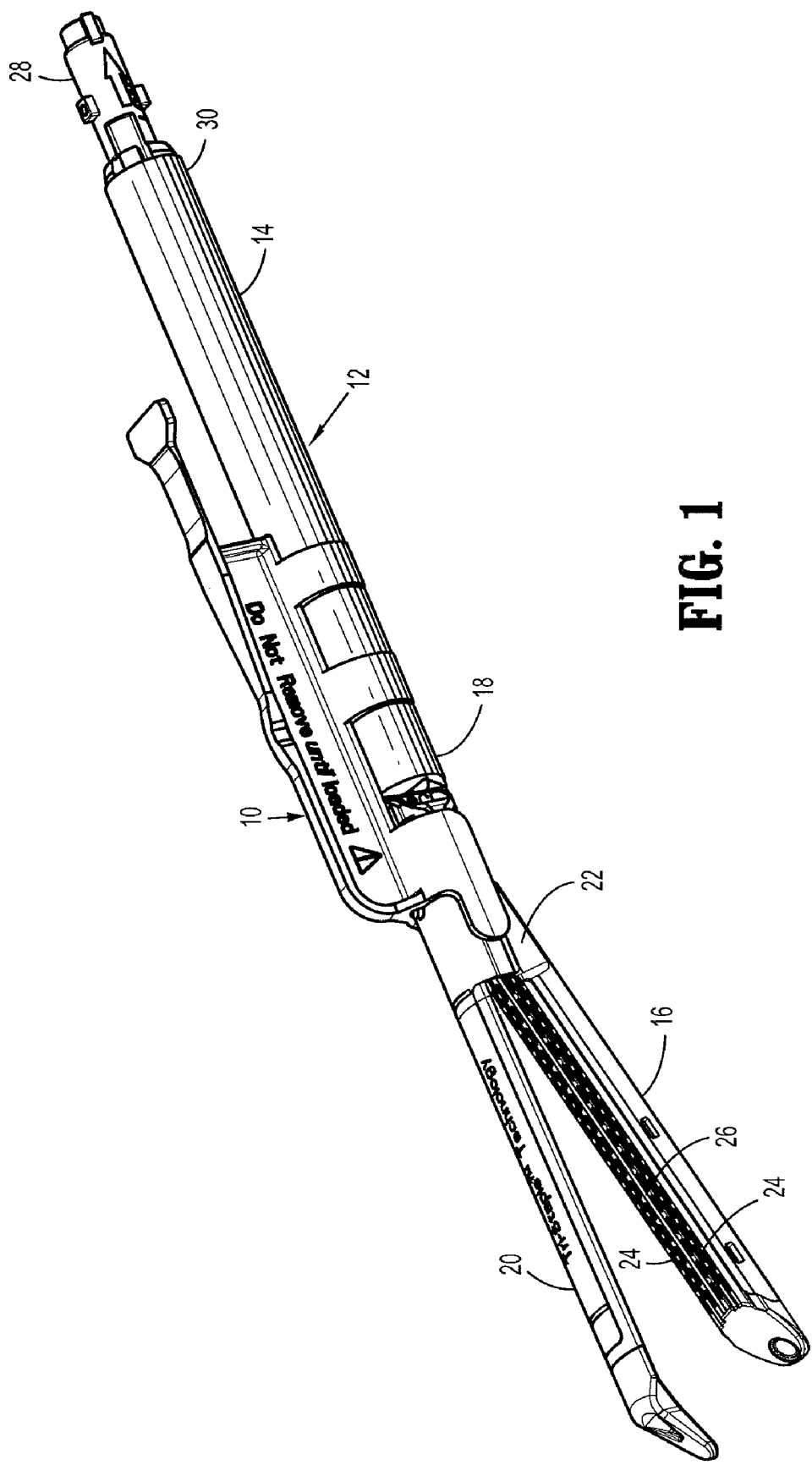
FIG. 1 is a perspective view of an embodiment of a shipping wedge with lockout ("shipping wedge") installed on a Single Use Loading Unit ("SULU")

Referring initially to FIG. 1, there is disclosed a surgical stapling instrument 10 according to an embodiment of the present disclosure. The instrument has a Loading Unit 12, e.g. a "SULU", and a shipping wedge or loading lock 10. The loading unit 12 is provided as a self contained, replaceable device which is removably attachable to the surgical stapling instrument in order to allow for multiple uses of the surgical stapling instrument. Loading unit 12 generally includes an elongate tubular member 14 having a staple cartridge 16 mounted to a distal end 18 of elongate tubular member 14. An anvil member 20 extends from and is affixed to distal end 18 of elongate tubular member 14. Staple cartridge 16 is movable from an open position spaced from anvil member 20 to a closed position in close cooperative alignment with anvil member 20 to clamp tissue therebetween. Specifically, a proximal end 22 of staple cartridge 16 is movably mounted to distal end 18 of elongate tubular member 14. Staple cartridge 16 is movable between the open and closed position in response to operation of an actuator (not shown) associated with the surgical stapling instrument.

Staple cartridge 16 includes pluralities of rows of staple containing pockets 24. Staples (not shown) contained in rows of staple containing pockets 24 are ejected out of staple cartridge 16, through tissue, and crimped against anvil member 20 in response to operation of an actuator such as a movable handle trigger. In order to accommodate a knife blade to sever the stapled tissue, staple cartridge 16 includes a longitudinal knife slot 26 extending between plurality of rows of staple containing pockets 24. Knife slot 26 allows for passage of the knife blade (see FIGS. 21 and 22) through the stapled tissue. When installed on loading unit 12, shipping wedge 10 prevents movement of the knife blade through knife slot 26 in a manner described hereinbelow.

A connector assembly 28 extends from a proximal end 30 of elongate tubular member 14 and is provided to allow loading unit 12 to be operatively connected to the surgical stapling instrument.

Figure 2:
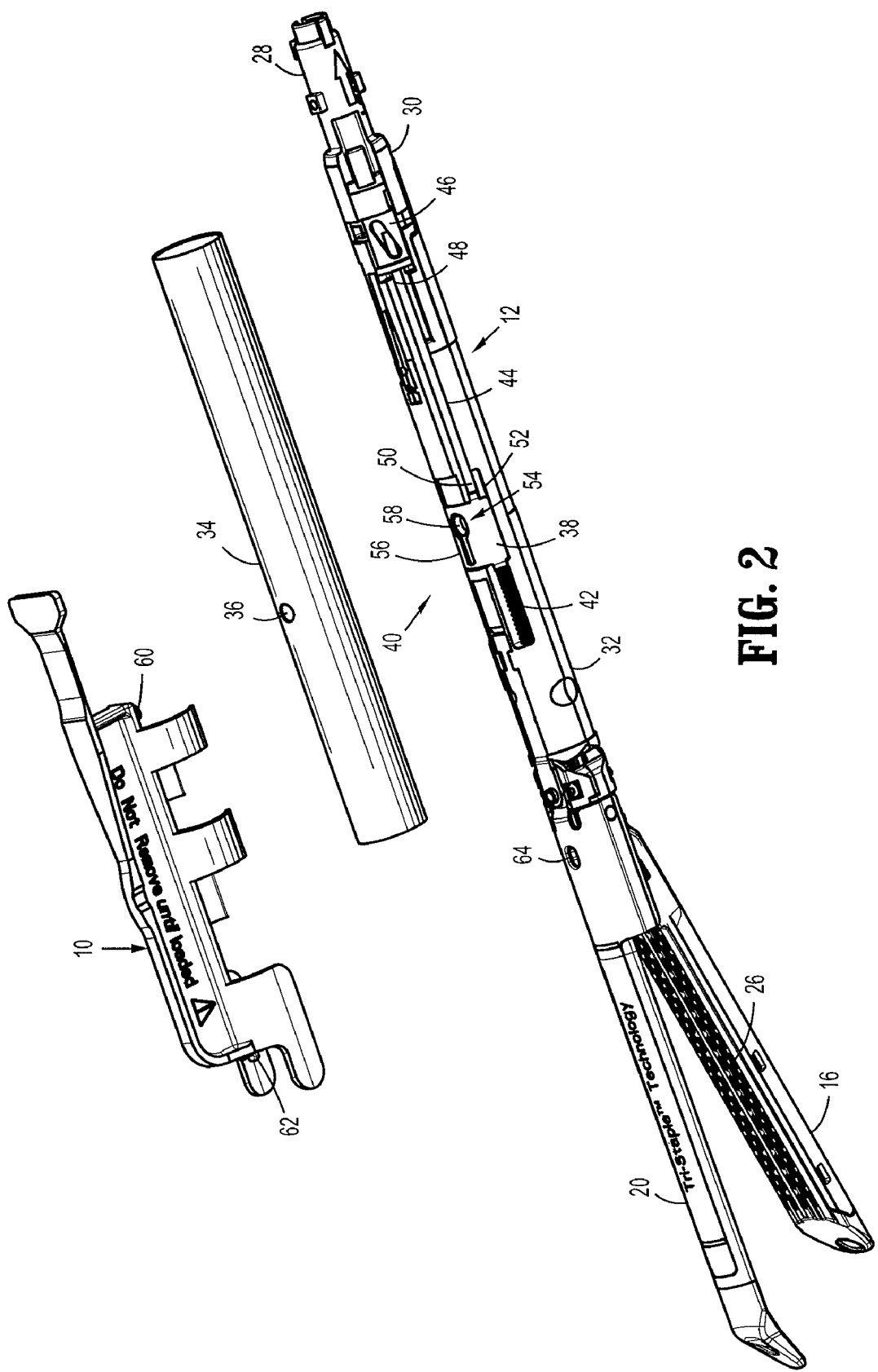
FIG. 2 is a perspective view of the shipping wedge and SULU with parts separated.
Figure 3:
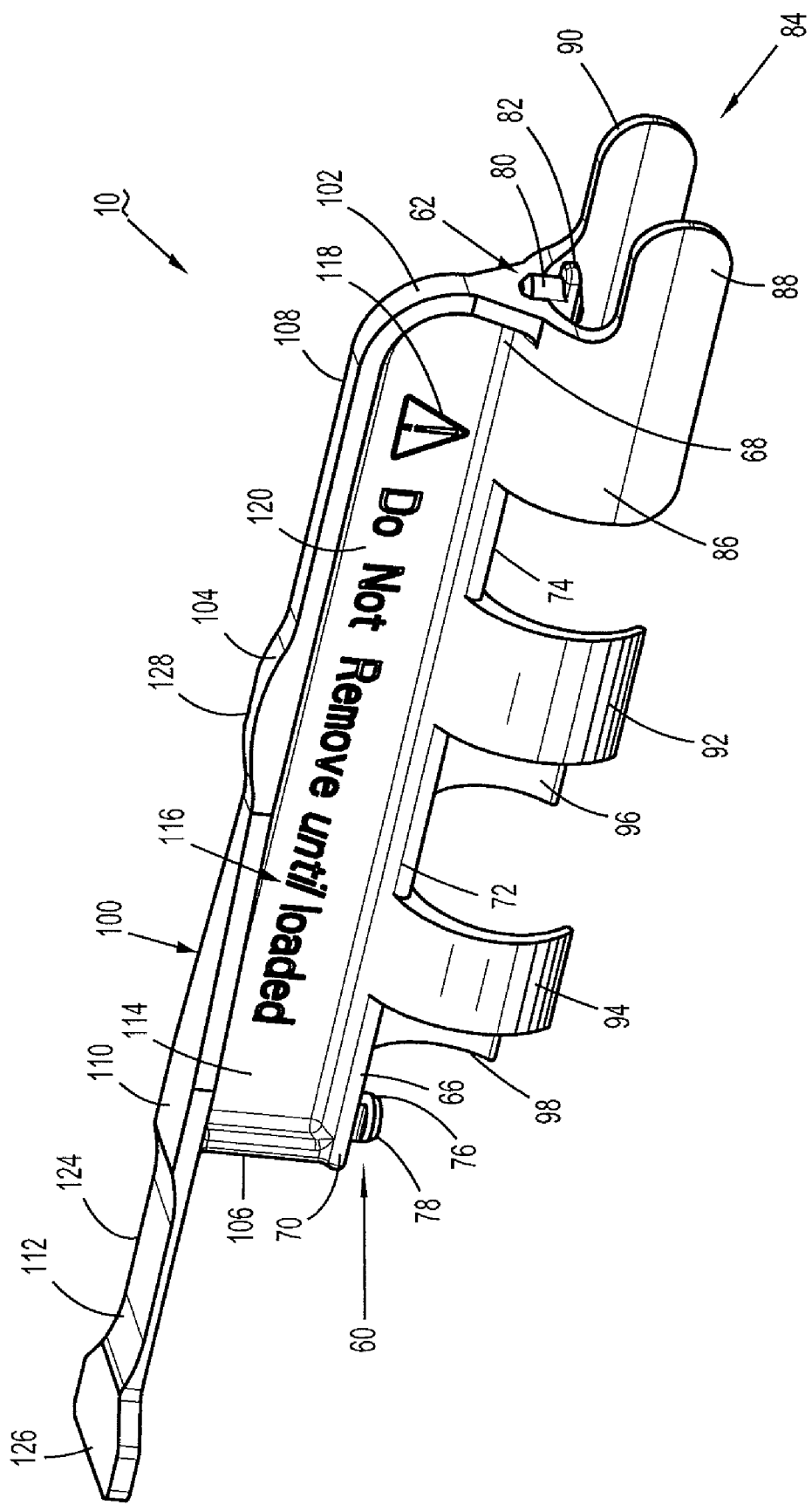
FIG. 3 is a perspective view of the shipping wedge.
Figure 4:
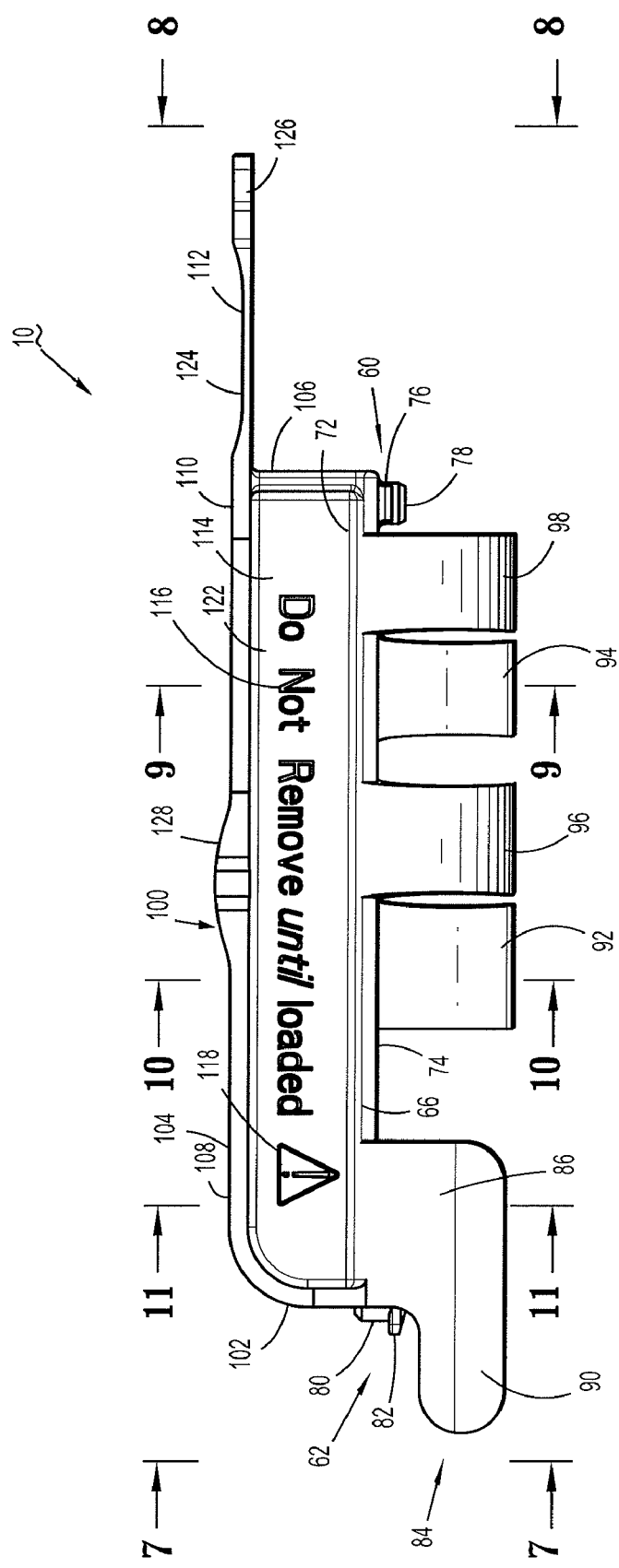
FIG. 4 is a side plan view of the shipping wedge.
Figure 5:
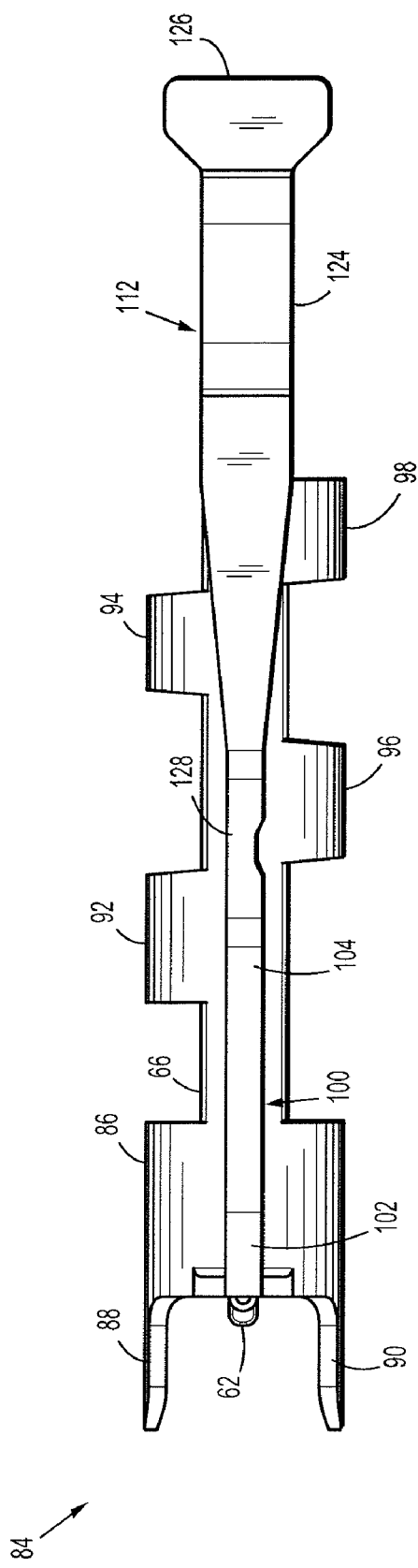
FIG. 5 is a top plan view of the shipping wedge.
Figure 6:
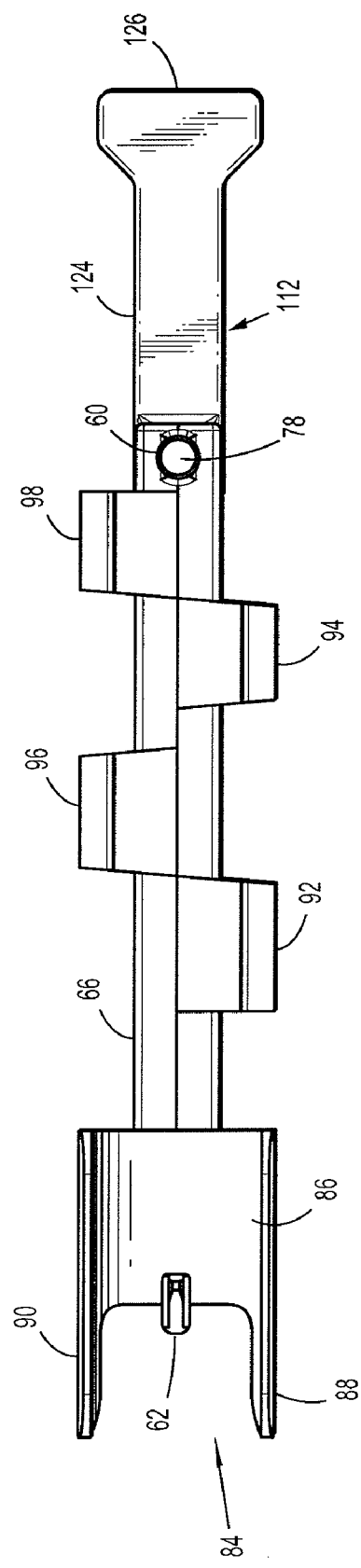
FIG. 6 is a bottom plan view of the shipping wedge.

Referring now to FIG. 2, loading unit 12 includes a body portion 32 having a cover tube 34 overlying body portion 32. A hole 36 is provided through cover tube 34 and functions with a locking plate 38, movably mounted on body portion 32, to form part of a locking mechanism 40 which prevents removal of shipping wedge 10 from elongate tubular member 14 prior to installation of loading unit 12 on a surgical stapling instrument. Locking mechanism 40 additionally includes a biasing or compression spring 42 to bias locking plate 38 proximally relative to body portion 32. An extension rod 44 abuts locking plate 38 and extends along body portion 32 from an actuator 46 on body portion 32. Specifically, a proximal end 48 of extension rod 44 engages actuator 46 while a distal end 50 of extension rod 44 engages a proximal edge 52 of locking plate 38. Movement of actuator 46 distally drives extension rod 44 and locking plate 38 distally along body portion 32 against the bias of compression spring 42.

Locking plate 38 includes a key hole slot 54 having a distal longitudinal keyway 56 and a proximal hole 58. Shipping wedge 10 includes a proximal locking pin 60 which is insertable through hole 36 in cover tube 34 and into key hole slot 54 in locking plate 38. Engagement of key way 56 of locking plate 38 with proximal locking pin 60 secures shipping wedge 10 against loading unit 12 until loading unit 12 has been properly installed into a surgical stapling instrument or until actuator 46 has been manually moved in a manner described in more detail hereinbelow. Shipping wedge or loading lock 10 additionally includes a distal hook 62 which is insertable through a hole 64 formed through distal end 18 of elongate tubular member 14 and serves to block movement of a knife 17 (see FIG. 17) through knife slot 26 in staple cartridge 16 when shipping wedge 10 is installed on loading unit 12.

Referring now to FIGS. 3-11, and initially with regard to FIGS. 3-6, the details of shipping wedge 10 will now be described. Shipping wedge 10 includes a generally elongate rectangular base 66 having a distal end 68, a proximal end 70, an upper surface 72 and a lower surface 74. Proximal locking pin 60 projects from lower surface 74 at proximal end 70 of base 66 while distal hook 62 projects from lower surface 74 at distal end 72 of base 66. With specific reference to FIGS. 3 and 4, proximal locking pin 60 includes a downward extension 76 extending from lower surface of 74 of base 66. Downward extension 76 terminates in an enlarged, circular locking flange 78. Distal hook 62 also has a downward extension 80 which terminates in a distally projecting lip 82. Locking flange 78 is positionable through hole 36 in cover tube 34 and hole 58 in key hole slot 54 of locking plate 38 while distally projecting lip 82 is insertable into hole 64 in elongate tubular member 14 (see also FIG. 2).

In order to initially position distal hook 62 relative to hole 64 in elongate tubular member 14 (FIG. 2), shipping wedge 10 includes a distally projecting, semi-cylindrical alignment unit 84. Alignment unit 84 includes a semi-cylindrical proximal portion 86 and a pair of distally extending alignment arms 88 and 90 extending distally from proximal portion 86. Proximal portion 86 and alignment arms 88 and 90 are relatively flexible so as to engage elongate tubular member 14 in snap fit fashion.

Referring to FIGS. 3-6, in order to further secure shipping wedge 10 on elongate tubular member 14 in snap fit fashion, shipping wedge 10 includes flexible hole arms 92, 94, 96 and 98 projecting downwardly from base 66. The flexible arms are shaped to cooperate with the cover tube and body portion. Flexible arms 92, 94, 96 and 98 are arcuate in shape and spaced longitudinally along base 66. For example, flexible arcuate arms 92 and 94 are longitudinally spaced along one side of base 66 while flexible arcuate arms 96 and 98 are spaced distally along an opposed side of base 66. In addition, flexible arcuate arms 92 and 94 are staggered longitudinally relative to flexible arcuate arms 96 and 98.

Shipping wedge 10 additionally includes a grasping frame 100 to facilitate manipulation of shipping wedge 10 onto elongate tubular member 14. Grasping frame 100 generally includes an arcuate distal portion 102, a central portion 104 and a proximal portion 106. Distal portion 102 extends from a distal end 108 of central portion 104 to distal end 68 of base 66. Likewise, proximal portion 106 extends from a proximal end 110 of central portion 104 to proximal end 70 of base 66. A thumb tab 112 extends proximally from proximal end 110 of central portion 104 to facilitate removal of shipping wedge 10 from elongate tubular member 14 in a manner described in more detail hereinbelow. An indicia plate 114 is provided between base 66 and grasping frame 100 and serves to strengthen or stiffen shipping wedge 10 as well as provide space for text and symbol indicia 116 and 118, respectively, on opposed sides 120 and 122 of indicia plate 114. Thumb tab 112 of shipping wedge 10 includes a flexible arm 124 terminating in an enlarged end 126. A central raised rib 128 is provided on central portion 104 of grasping frame 100.

Figure 7:
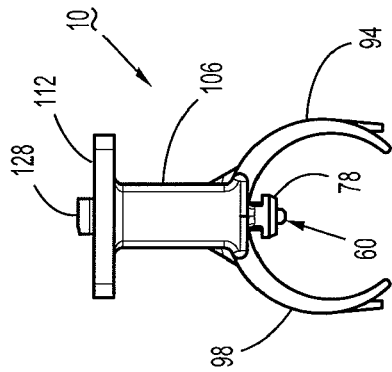
FIG. 7 is an end view taken along line 7-7 of FIG. 4.
Figure 8:
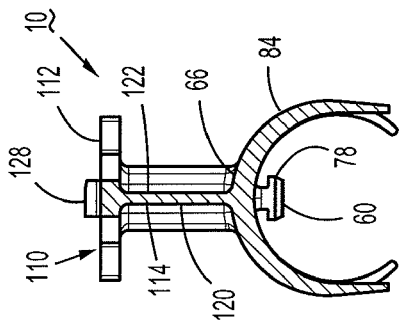
FIG. 8 is an opposite end view taken along line 8-8 of FIG. 4.

As best shown in FIG. 7, distal hook 62 projects downwardly through semicylindrical alignment unit 84 and between distally extending alignment arms 88 and 90. As best seen in FIG. 8, proximal locking pin 60, including circular locking flange 78, projects downwardly into the space defined by the flexible arcuate arms 94 and 98.

Shipping wedge 10 may be formed from a variety of relatively flexible materials such as, for example, polymeric materials, metallic materials, etc. Forming shipping wedge 10 from flexible materials allows alignment arms 88 and 90 of distally projecting alignment unit 84, as well as flexible arcuate arms 92, 94, 96 and 98, to flex outwardly around loading unit 12 to allow shipping wedge 10 to be attached to loading unit 12 in snap fit fashion. Similarly, the flexible nature of the materials forming shipping wedge 10 allows thumb tab 112 to flex slightly to facilitate removal of shipping wedge 10 from loading unit 12. As noted herein above, shipping wedge 10 includes base 66 which, in conjunction with grasping frame 100 and indicia plate 114, provides sufficient rigidity to shipping wedge 10 in order to prevent undue flexing and inadvertent dislodgement of shipping wedge 10 from loading unit 12.

Figure 9:
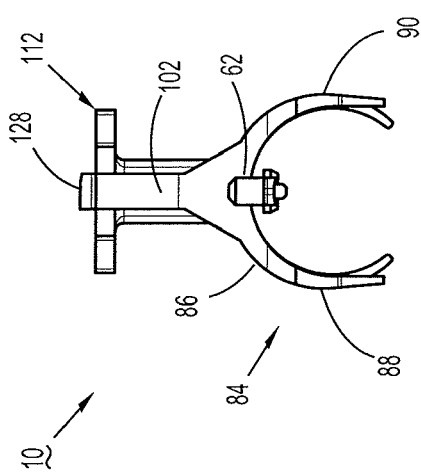
FIG. 9 is a cross-sectional view taken along line 9-9 of FIG. 4.
Figure 10:
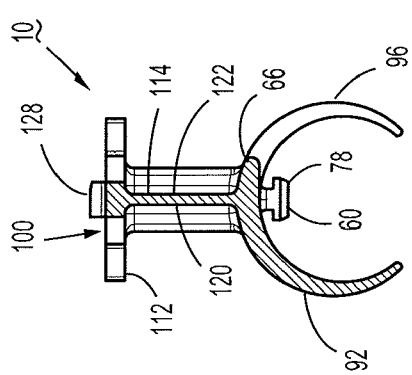
FIG. 10 is a cross-sectional view taken along line 10-10 of FIG. 4.
Figure 11:
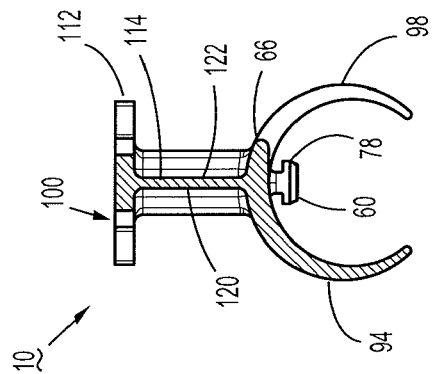
FIG. 11 is a cross-sectional view taken along line 11-11 of FIG. 4.

The elements of shipping wedge 10 may be formed from a variety of separate components which are then welded, glued or otherwise assembled or, with specific reference to FIGS. 9-11, shipping wedge 10 may be formed integrally as one single, monolithic molded or machined unit. For example, as shown in FIG. 9, flexible arcuate arm 94 is illustrated integral with indicia plate 114 and grasping frame 100 while in FIG. 10, flexible arcuate arm 92 is illustrated integral with indicia plate 114 and grasping frame 100. As best shown in FIG. 11, distally projecting alignment unit 84 is illustrated as being formed integral with indicia plate 114 and grasping frame 110.

Figure 12:
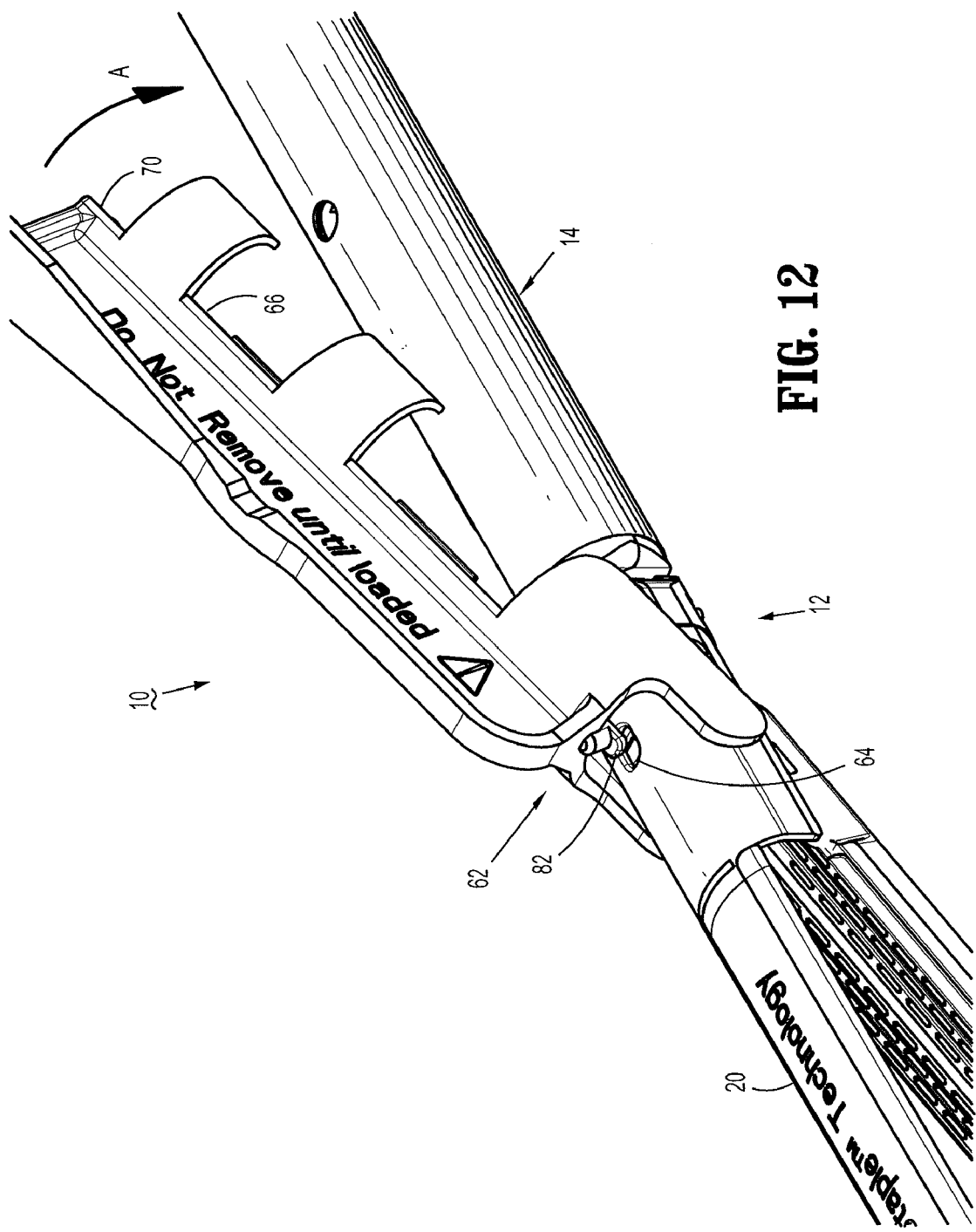
FIG. 12 is a perspective view illustrating a distal end of the shipping wedge during initial installation into the SULU.
Figure 13:
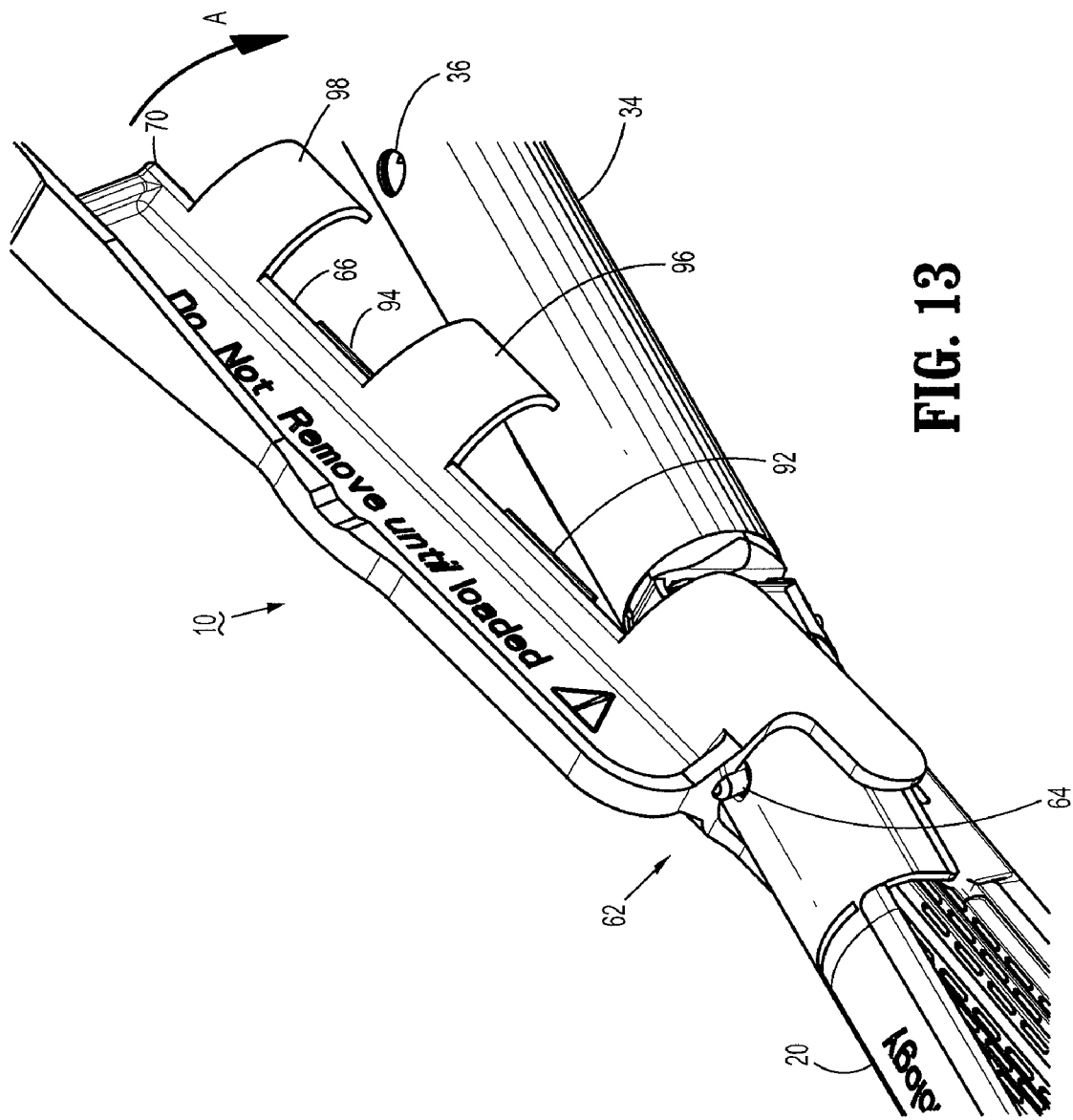
FIG. 13 a perspective view similar to FIG. 12 illustrating further installation of the shipping wedge into the SULU.
Figure 14:
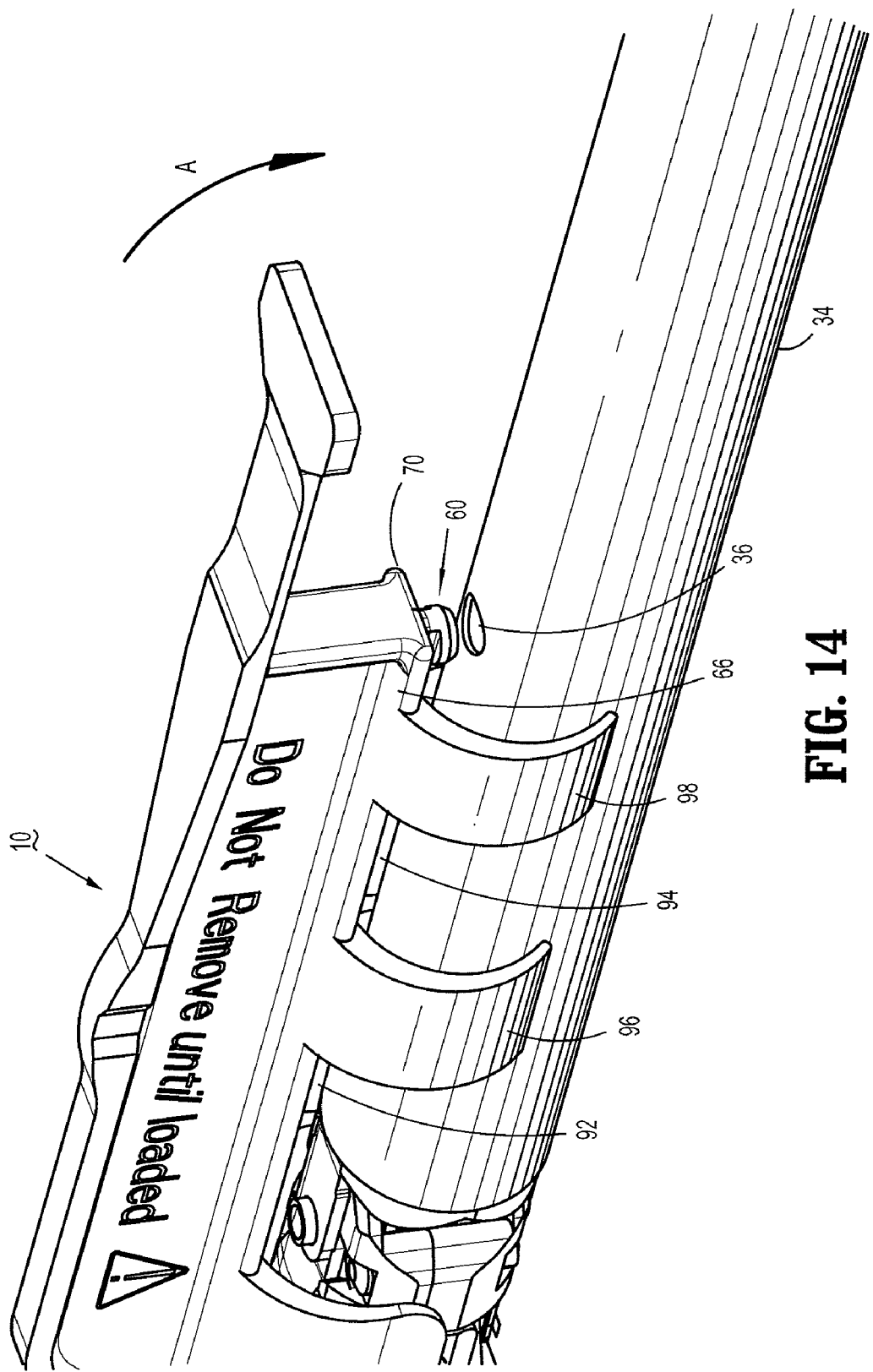
FIG. 14 is a perspective view of a proximal end of the shipping wedge positioned adjacent the SULU.

Referring now to FIGS. 2, 3 and 12-22, the use of shipping wedge 10 in conjunction with lockout mechanism 40 on loading unit 12 will now be described. Referring initially to FIGS. 12 and 13, in order to assemble shipping wedge 10 to loading unit 12, shipping wedge 10 is initially positioned adjacent loading unit 12 such that alignment arms 88 and 90 surround anvil 20 and distal hook 62 of shipping wedge 10 is positioned over hole 64 in anvil 20. Shipping wedge or loading lock 10 is then manipulated such that distally projecting lip 82 of distal hook 62 enters hole 64 (FIG. 13). Thereafter, with reference to FIGS. 12-14, proximal end 70 of base 66 is pivoted downwardly in the direction of arrow A, causing flexible arcuate arms 92, 94, 96 and 98 to engage and flex around cover tube 34 of loading unit 12. As noted herein above, flexible arcuate arms 92, 94, 96 and 98 are provided to secure shipping wedge 10 against loading unit 12 and prevent shipping wedge 10 from inadvertently falling off loading unit 12. With specific reference to FIG. 14, in this condition, proximal locking pin 60 of shipping wedge 10 is positioned adjacent hole 36 in cover tube 34.

Figure 15:
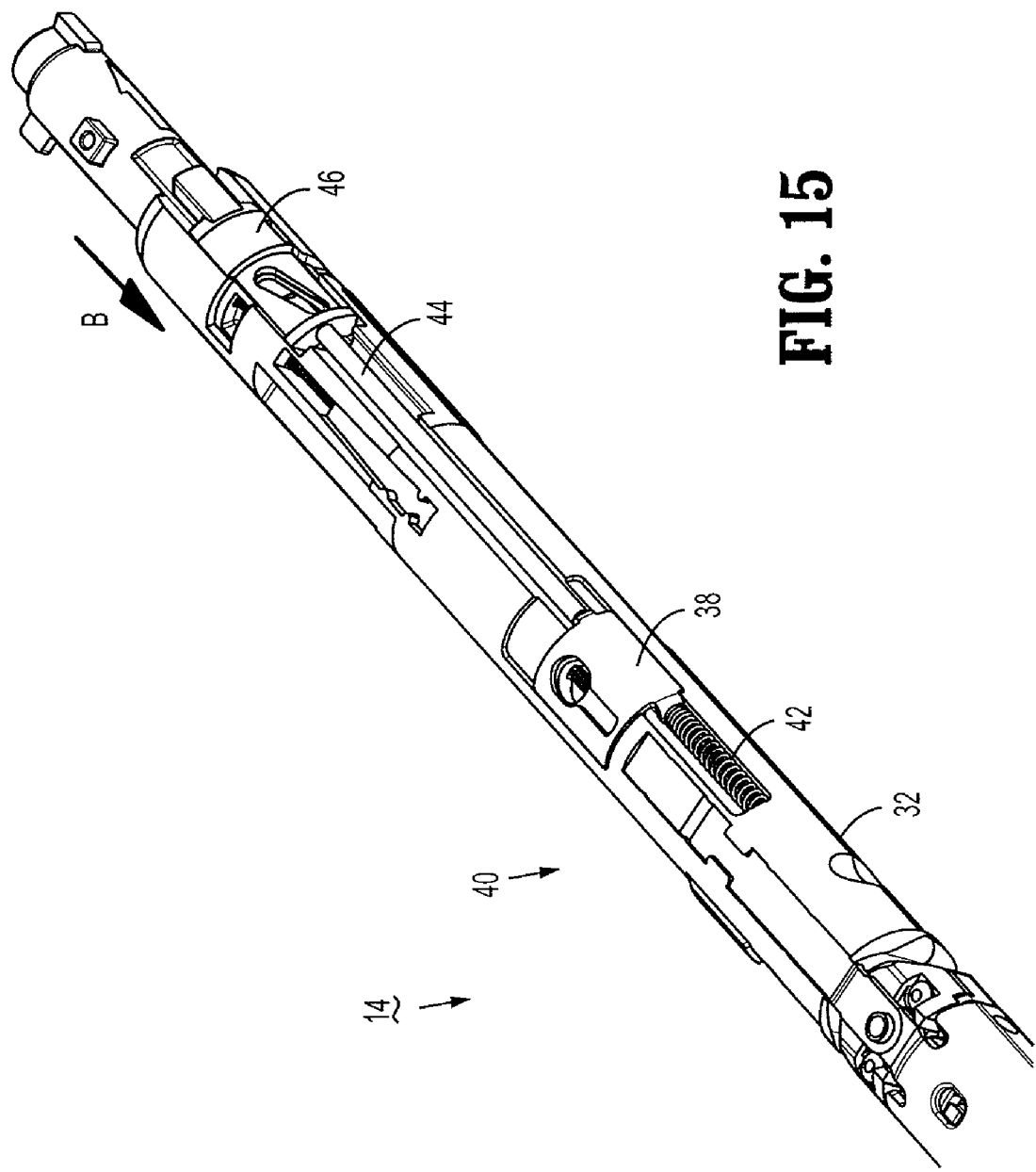
FIG. 15 is a perspective view of the SULU with a cover tube removed.
Figure 16:
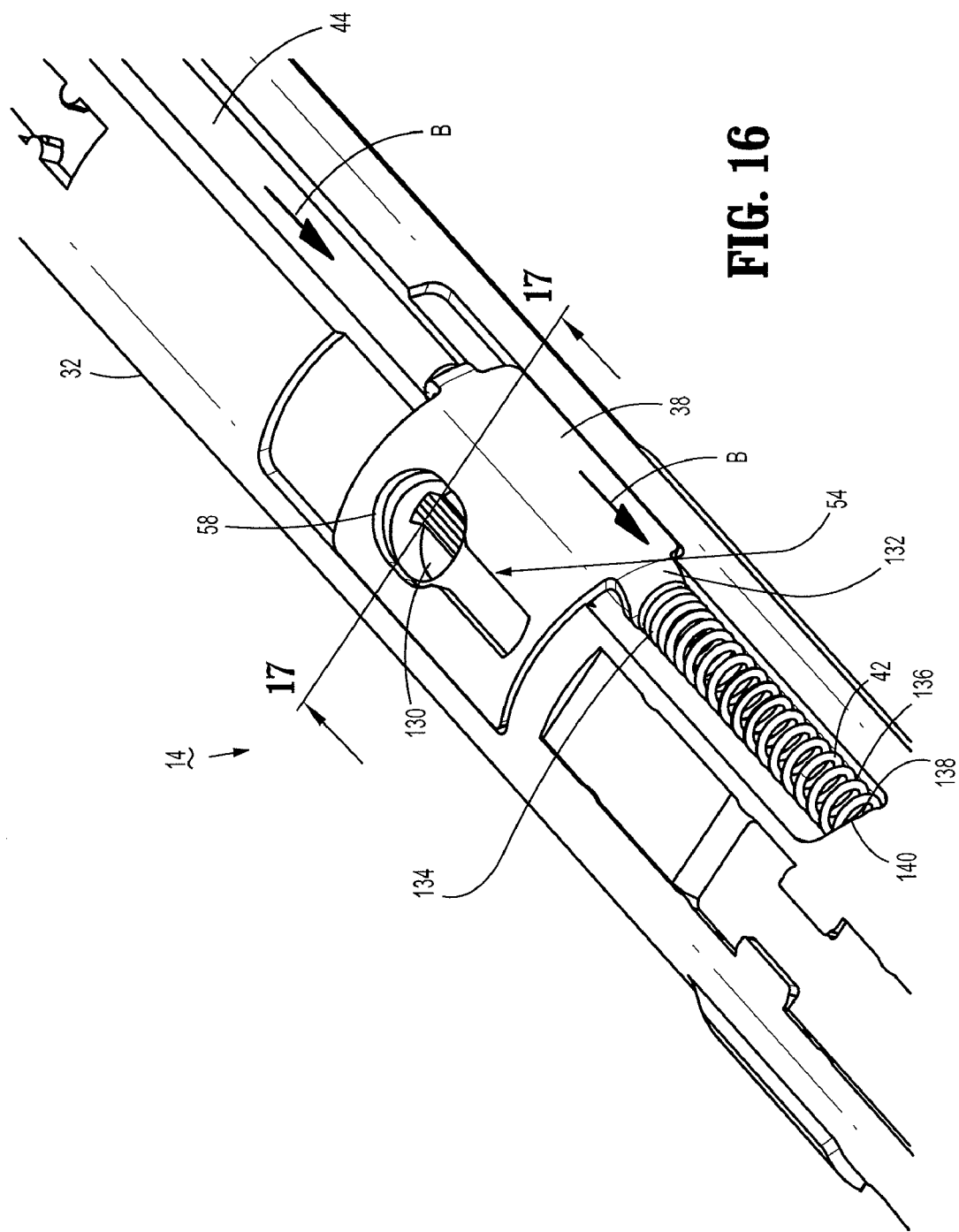
FIG. 16 is an enlarged perspective view of the SULU illustrating a locking mechanism in an unlocked position on the SULU.

Referring to FIGS. 15 and 16, during the initial or factory installation of shipping wedge 10 to loading unit 14, locking mechanism 40 is artificially manipulated into an unlocked condition by advancing actuator 46 distally in the direction of arrow B. Movement of actuator 46 distally drives extension rod 44 and locking plate 38 distally relative to body portion 32 of elongate tubular member 14 and against the bias of compression spring 42. As specifically shown in FIG. 16, when locking plate 38 is in the distal most position relative to body portion 32 of elongate tubular member 14, hole 58 of key hole slot 54 in locking plate 38 is positioned directly above a depression 130 formed in body portion 32 of elongate tubular member 14. As further best shown in FIG. 16, locking plate 38 includes a distal arm 132 which engages a proximal end 134 of compression spring 42. Compression spring 42 is constrained within a spring trough 136 formed in body portion 32. A distal end 138 of compression spring 42 abuts a distal end 140 of spring trough 136.

Figure 17:
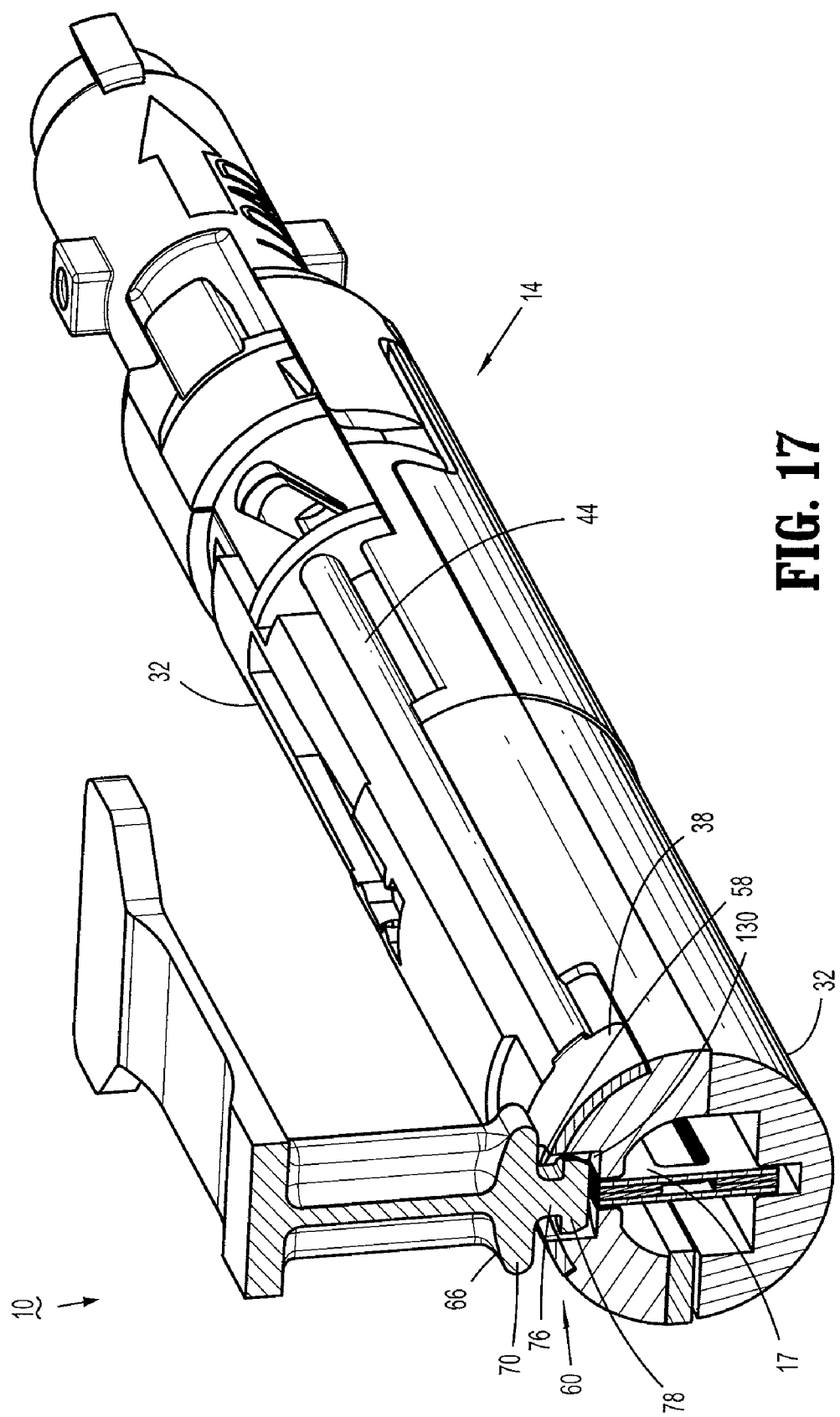
FIG. 17 is a cross-sectional view taken along line 17-17 of FIG. 16 with the shipping wedge installed through the locking mechanism.

With specific reference now to FIG. 17, once shipping wedge 10 has been fully manipulated in the direction of the arrow A to bring flexible arcuate arms 92, 94, 96 and 98 into engagement with cover tube 34 (FIG. 14), proximal locking pin 60 of shipping wedge 10 is seated in depression 130 in body portion 32 of elongate tubular member 14 such that circular locking flange 78 of proximal locking pin 60 is within depression 130 and downward extension 76 of proximal locking pin 60 is positioned within hole 58 of key hole slot 54 in locking plate 38. In this position, locking plate 38 is in the distal most or unlocked condition enabling proximal locking pin 60 of shipping wedge 10 to be inserted and subsequently removed through keyhole slot 54 of locking plate 38.

Figure 18:
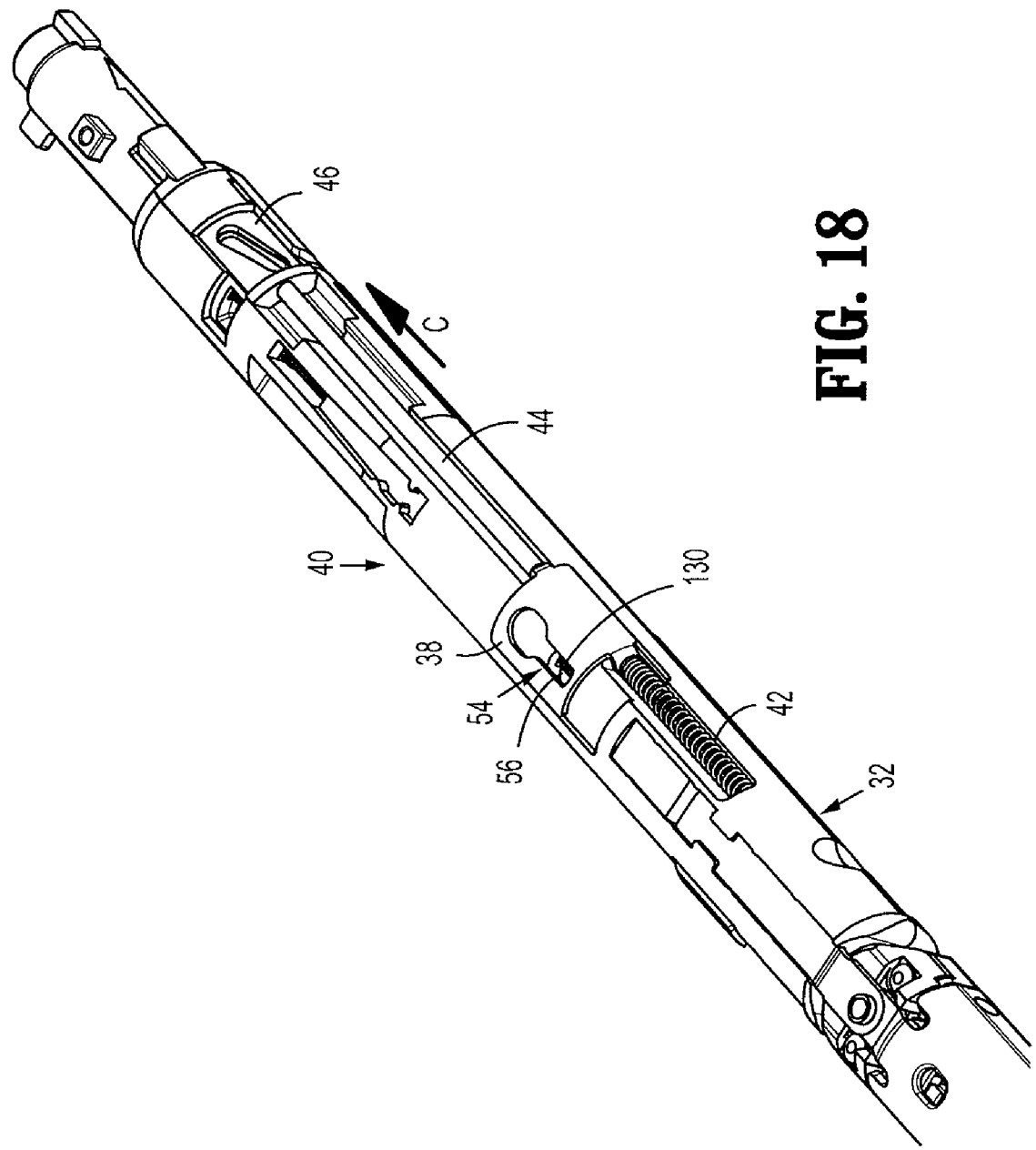
FIG. 18 is a perspective view similar to FIG. 15 with the locking mechanism in a locked position.
Figure 19:
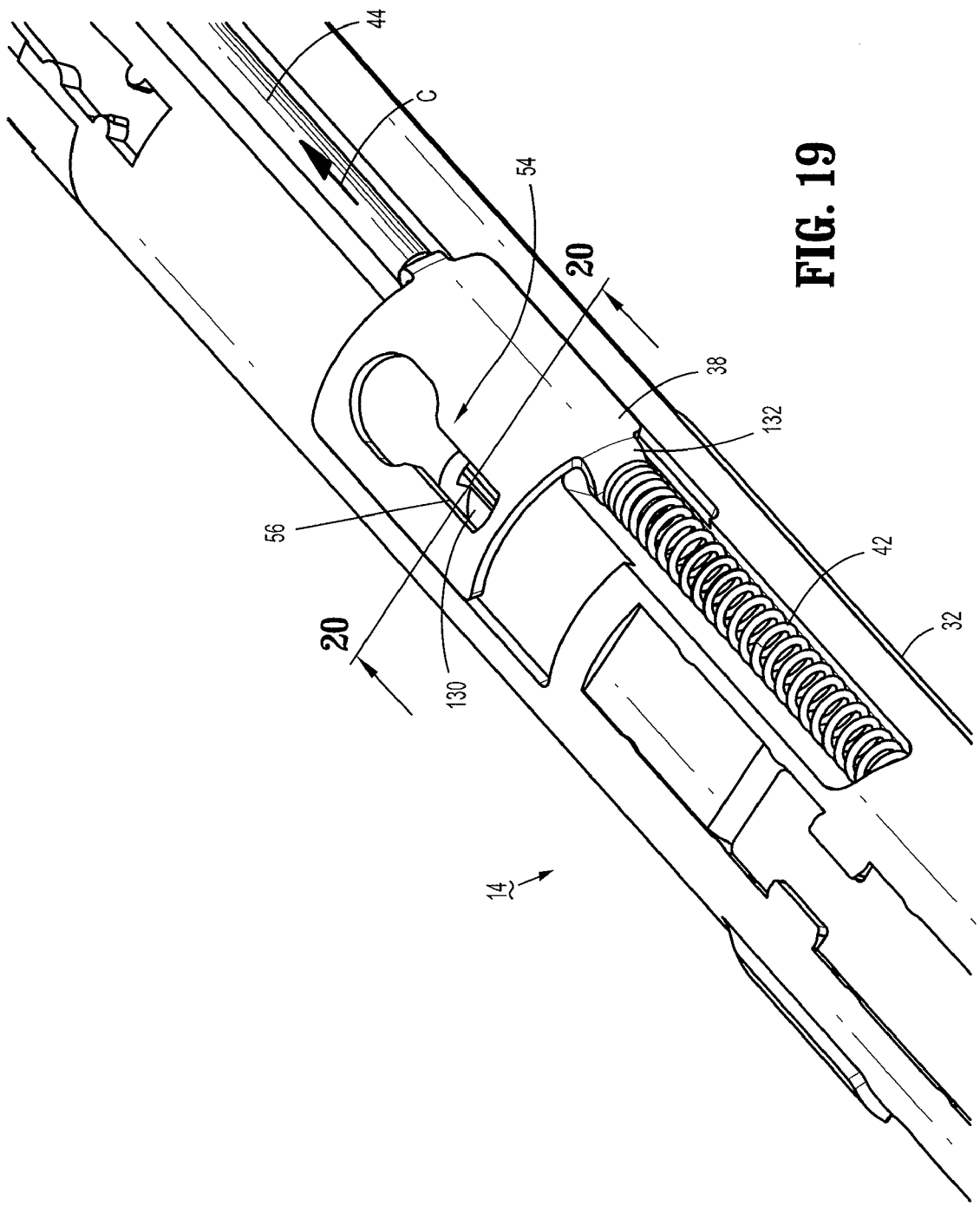
FIG. 19 is an enlarged perspective view similar to FIG. 16 with the locking mechanism in the locked position.

Referring now to FIGS. 18 and 19, in order to move locking plate 38 into a locked condition distal pressure is removed from actuator 46 allowing lockout mechanism 40, including extension rod 44 and lockout plate 38 to move proximally in the direction of arrow C against the bias of compression spring 42. As specifically shown in FIG. 19, when locking plate 38 is in a proximal most position, narrower width keyway 56 of keyhole slot 54 is located over depression 130 formed a body portion 32 of elongate tubular member 14.

Figure 20:
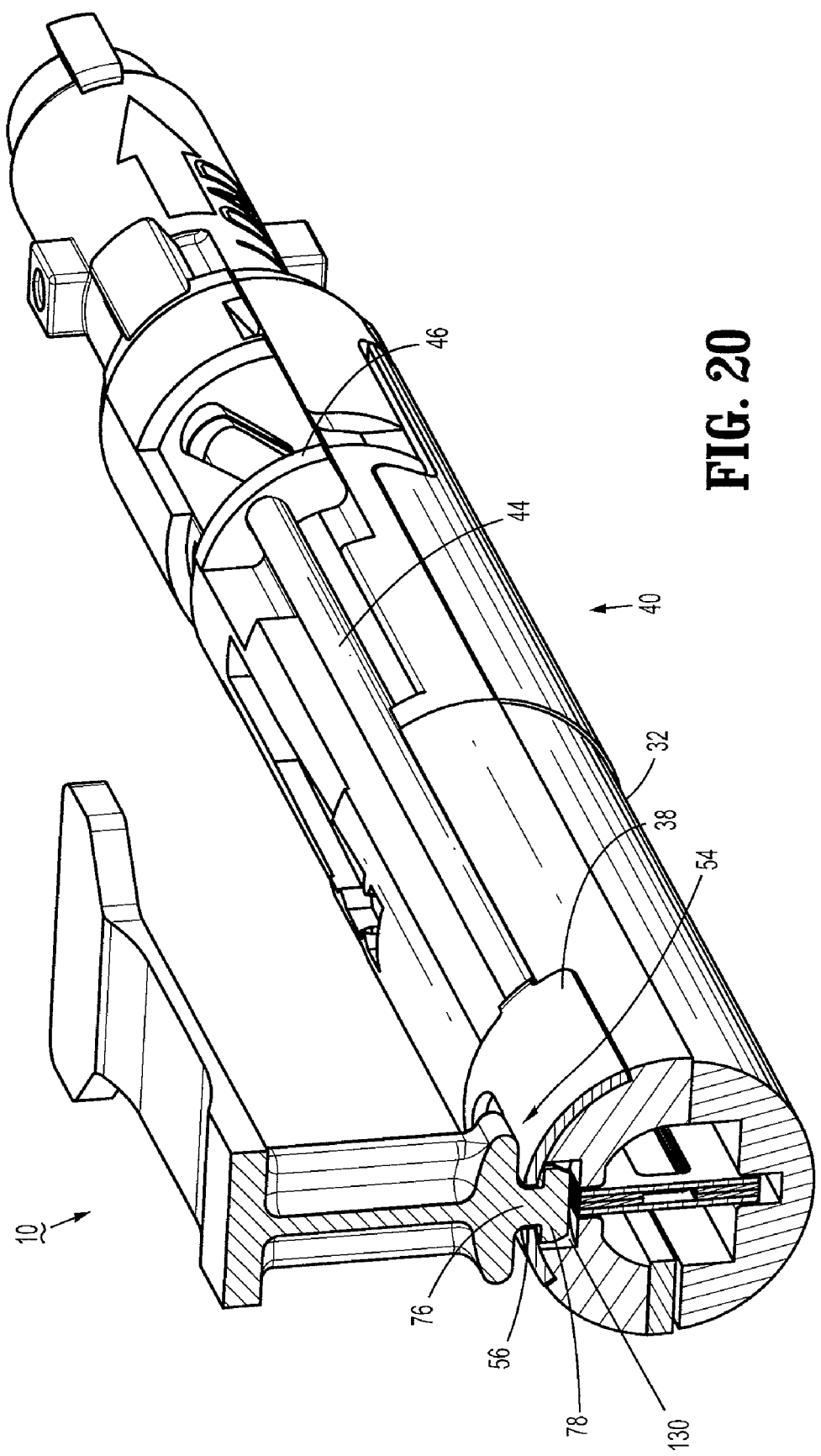
FIG. 20 is a cross-sectional view taken along line 20-20 of FIG. 19 with the shipping wedge in the locked condition.

With reference to FIG. 20, it can be seen that with locking plate 38 of lockout mechanism 40 in a proximal or a locked position, downward extension 76 of proximal locking pin 60 is positioned within keyway 56 of keyhole slot 54. Circular locking flange 78 of proximal locking pin 60, being larger in diameter than the width of keyway 56 in keyhole slot 54, prevents removal of proximal locking pin 60 out of depression 130 formed in body portion 32. This prevents shipping wedge 10 from being removed from body portion 32 and, in turn, loading unit 14 when locking mechanism 40, and specifically locking plate 38, is in the distal most or locked condition. In this manner, locking mechanism 40 completely prevents removal of shipping wedge 10 from loading unit 12 until such time as locking mechanism 40 has been moved to the unlocked condition either artificially during initial assembly of shipping wedge 10 to loading unit 12 or, more importantly, during movement of actuator 46 distally by installation of loading unit 12 fully into a surgical stapling instrument.

Figure 21:
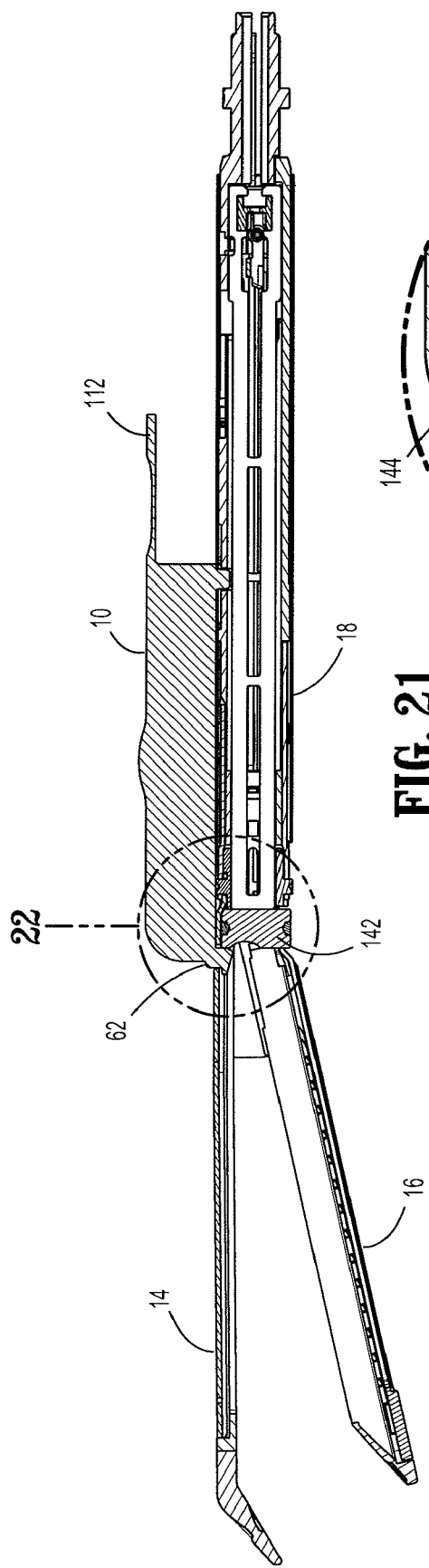
FIG. 21 is a cross-sectional view of the shipping wedge installed on the SULU and in the locked condition.
Figure 22:
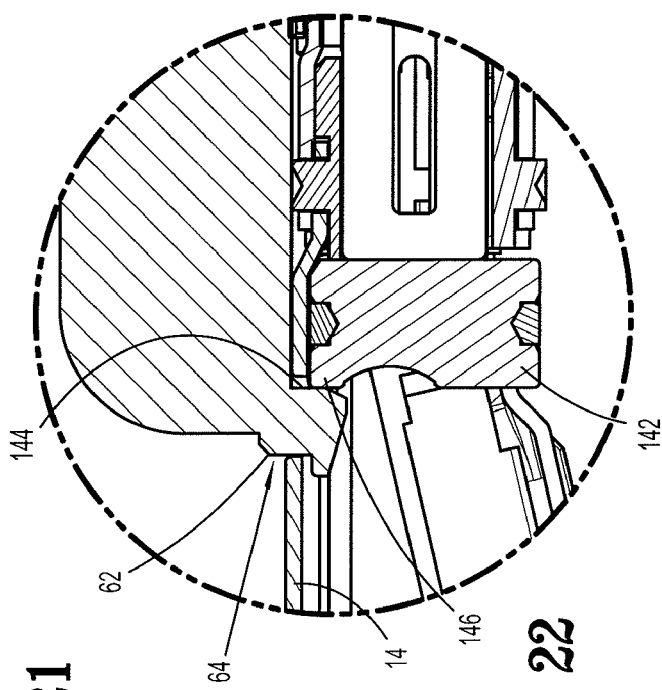
FIG. 22 is an enlarged area of detail view of FIG. 21 illustrating a distal shipping hook engaged with the SULU and blocking a knife blade of the SULU.

Referring finally to FIGS. 21 and 22, and as noted herein above, shipping wedge 10, and in particular distal hook 62 of shipping wedge 10, is provided to prevent inadvertent and premature movement or advancement of a knife blade 142 included in loading unit 12 distally within elongate tubular member 14. As best shown in FIG. 22, with distal hook 62 positioned through hole 64 in elongate tubular member 14, a proximal end 144 of distal hook 62 blocks distal movement of knife blade 142 by engagement with a distal end 146 of knife blade 142.

It will be understood that various modifications may be made to the embodiments disclosed herein. For example, the locking pin on the shipping wedge or loading lock may have alternative shapes, such as, for example T-shaped, etc. Further, the locking pin may be engaged by an edge of the locking plate. Additionally, the distal hook of the shipping wedge or loading lock may engage alternate components on the SULU such as, for example, driving bars for ejecting the staples, etc. The loading unit shown in FIG. 1 has a staple cartridge and an anvil. However, surgical instruments having staple cartridges that are removable and replaceable are also contemplated. Therefore, the above description should not be construed as limiting, but merely as exemplifications of particular embodiments. Those skilled in the art will envision other modifications within the scope and spirit of the claims appended hereto.

The invention claimed is:

1. A shipping wedge for use with a surgical instrument having a body portion comprising:
   a base;
   a blocking member depending from the base and engagable with a movable operative member of the surgical instrument;
   flexible arms projecting from the base and being shaped to cooperate with the body portion of the surgical instrument; and
   a locking member depending from the base and engageable with a lockout mechanism of the surgical instrument.

2. The shipping wedge as recited in claim 1, wherein the locking member includes an enlarged flange.

3. The shipping wedge as recited in claim 2, wherein the flange is a circular disc.

4. The shipping wedge as recited in claim 3, wherein the shipping wedge includes a downward extension connecting the circular disc to the base.

5. The shipping wedge as recited in claim 2, wherein the flexible arms are a first flexible arm and a second flexible arm depending from opposed sides of the base.

6. The shipping wedge as recited in claim 5, further comprising an alignment unit located at a distal end of the base and including a pair of distally projecting, flexible arms.

7. The shipping wedge as recited in claim 5, wherein the first and second flexible grasping arms are longitudinally spaced along the base.

8. The shipping wedge as recited in claim 7, further comprising second and third flexible arms depending from opposed sides of the base and longitudinally spaced from the first and second flexible arms.

9. The shipping wedge as recited in claim 6, further comprising a grasping frame extending from a side of the base opposite of the locked member.

10. The shipping wedge as recited in claim 9, further comprising an indicia plate located between the grasping frame and the base for display of various modes of informational indicia.

11. The shipping wedge as recited in claim 9, further comprising a flexible thumb tab extending from a proximal end of the grasping frame.

12. The shipping wedge as recited in claim 11, wherein the shipping wedge is formed from a polymeric material.

13. The shipping wedge as recited in claim 12, wherein the shipping wedge is integrally formed.

14. The shipping wedge as recited in claim 1, wherein the blocking member is a distally facing hook engageable with a movable operative member of the surgical instrument.

15. A surgical instrument having a lockout mechanism, comprising:
   a body portion;
   an actuator movably mounted on the body portion;
   a lockout mechanism including a locking plate movably mounted to the body portion;
   a loading lock having a locking member, the locking plate being engageable with the locking member of the loading lock, the locking plate being movable in response to movement of the actuator between a locked position preventing removal of the loading lock from the body portion to an unlocked position allowing removal of the loading lock from the body portion, the loading lock having flexible arms shaped to cooperate with the body portion of the surgical instrument.

16. The surgical instrument as recited in claim 15, wherein the locking plate includes a keyhole slot engageable with the loading lock, the keyhole slot including a first narrower locking portion and a second enlarged unlocking portion.

17. The surgical instrument as recited in claim 15, wherein the locking plate is operatively connected to the actuator by an extension rod.

18. The surgical instrument as recited in claim 17, wherein the locking plate is biased to the locked position by a biasing spring mounted in the body portion.

19. The surgical instrument as recited in claim 15, wherein the body portion has a knife member and the loading lock has a hook insertable through a hole defined in the body portion and arranged to block movement of the knife member.

20. A loading unit having a shipping safety device comprising:
   a body portion;
   a movable operative device disposed in the body portion;
   an actuator associated with the body portion and operable to move the movable operative device;
   a locking member movably mounted in the body portion and movable in response to movement of the actuator, the locking member movable between a first locked position and a second unlocked position;
   a removable safety device having a base;
   a blocking member projecting from the base and engageable with the movable operative device; and
   a lockout member projecting from the base and engageable with the locking member, wherein the removable safety device is locked to the body portion when the locking member is in the first locked position and is unlocked for removal from the body portion when the locking member it is in the second unlocked position.

* * * * *